United States Patent [19]

Bogert

[11] Patent Number: 5,562,631

[45] Date of Patent: Oct. 8, 1996

[54] CATHETER ARRANGEMENT WITH INTERLOCKING SEQUENCED GUARDING MEMBERS FOR PROTECTING CANNULA

[75] Inventor: David L. Bogert, Plainville, Conn.

[73] Assignee: Johnson & Johnson Medical, Inc., Arlington, Tex.

[21] Appl. No.: 483,950

[22] Filed: Jun. 7, 1995

[51] Int. Cl.[6] .................................................. A61M 5/00
[52] U.S. Cl. ............................................ 604/164; 604/263
[58] Field of Search .............................. 604/263, 198, 604/164, 165, 158, 51–53

[56] References Cited

U.S. PATENT DOCUMENTS

| | | | |
|---|---|---|---|
| 4,762,516 | 8/1988 | Luther et al. | 604/164 |
| 4,826,490 | 5/1989 | Byrne et al. | 604/198 |
| 4,846,805 | 7/1989 | Sitar | 604/165 |
| 4,917,669 | 4/1990 | Bonaldo | 604/164 |
| 4,950,252 | 8/1990 | Luther et al. | 604/198 |
| 5,084,030 | 1/1992 | Byrne et al. | 604/198 |
| 5,171,231 | 12/1992 | Heiliger | 604/263 |
| 5,215,528 | 6/1993 | Purdy et al. | 604/164 |
| 5,429,613 | 7/1995 | D'Amico | 604/198 |

*Primary Examiner*—John D. Yasko
*Attorney, Agent, or Firm*—Joseph F. Shirtz

[57] ABSTRACT

A catheter needle tip protector and a safety mechanism which provides fail-safe protection for clinical personnel against the possibility of accidental punctures by a used IV cannular needle through automatic catheter needle tip protecting structure operative upon withdrawal of the cannular from a venipuncture the body of a patient.

13 Claims, 10 Drawing Sheets

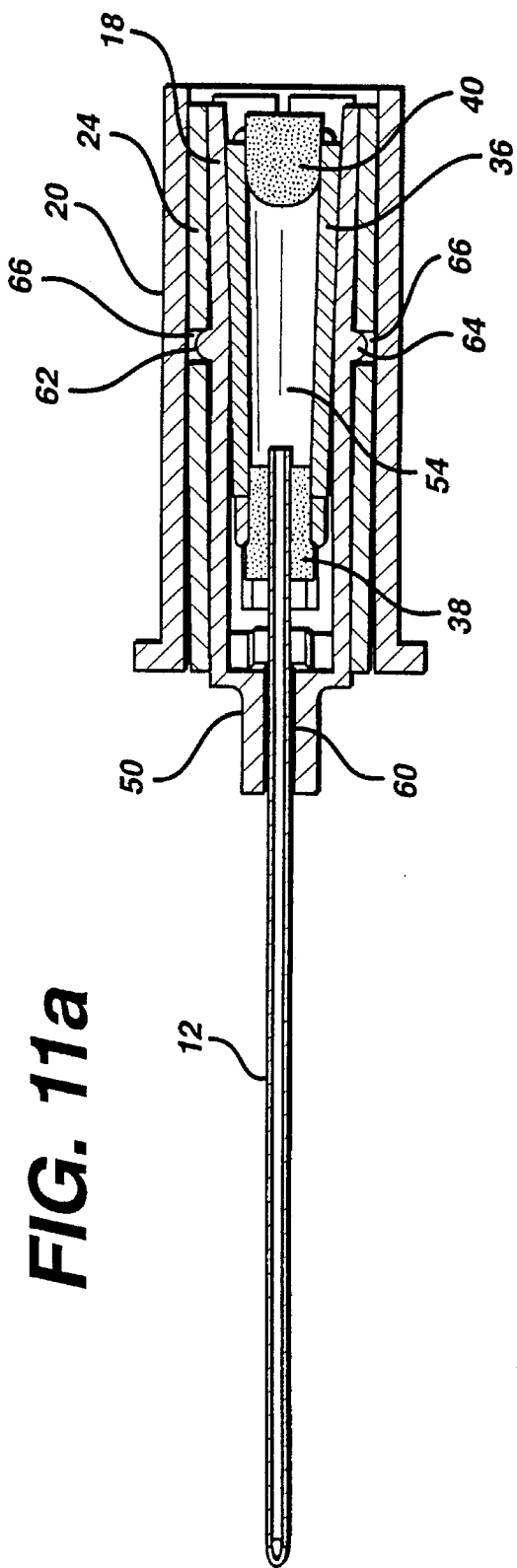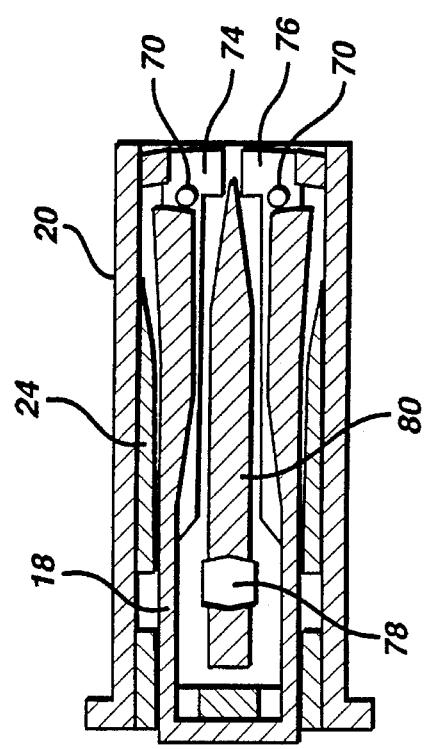

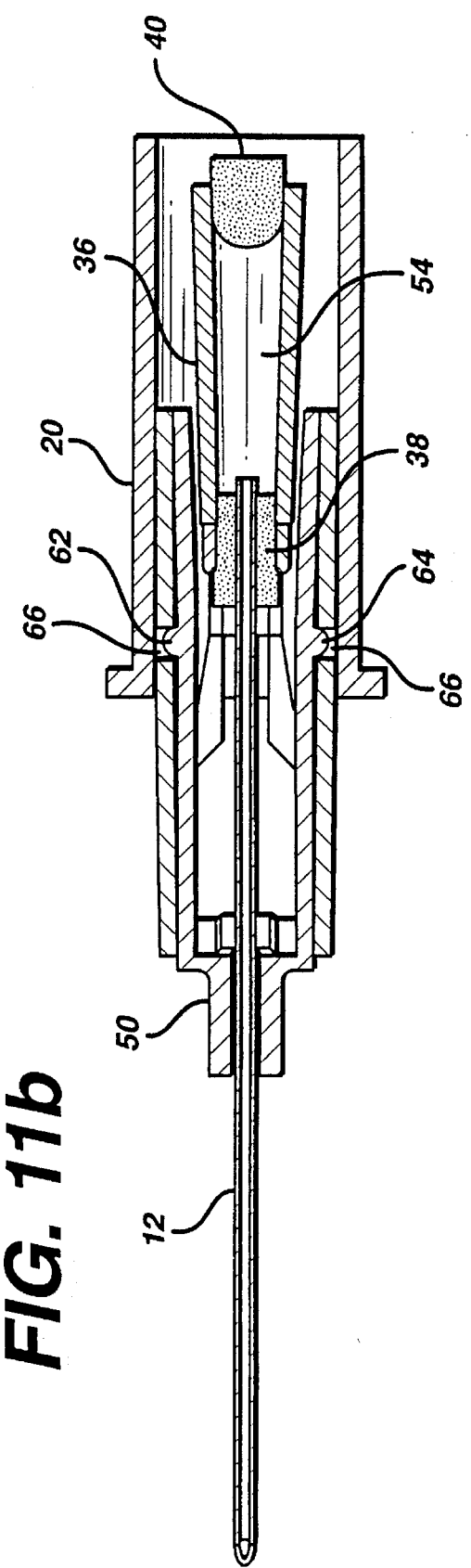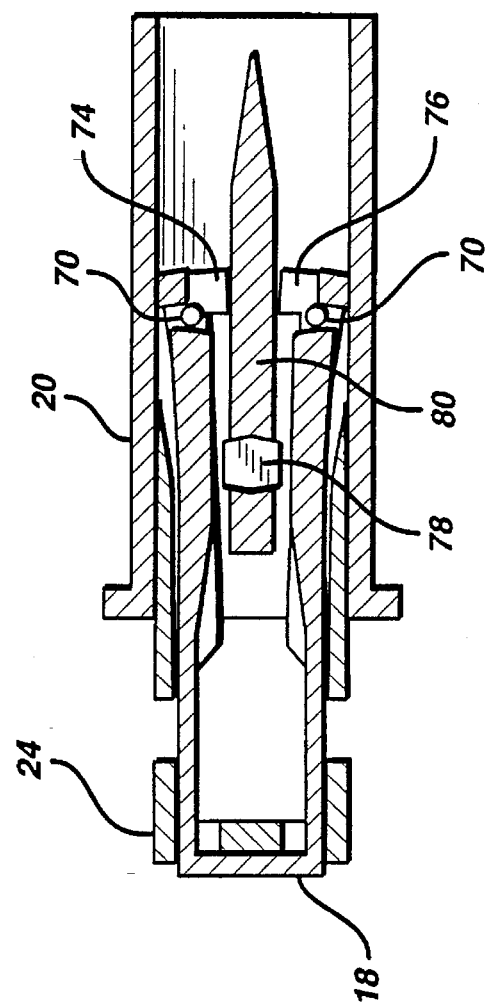
FIG. 11b
FIG. 12b

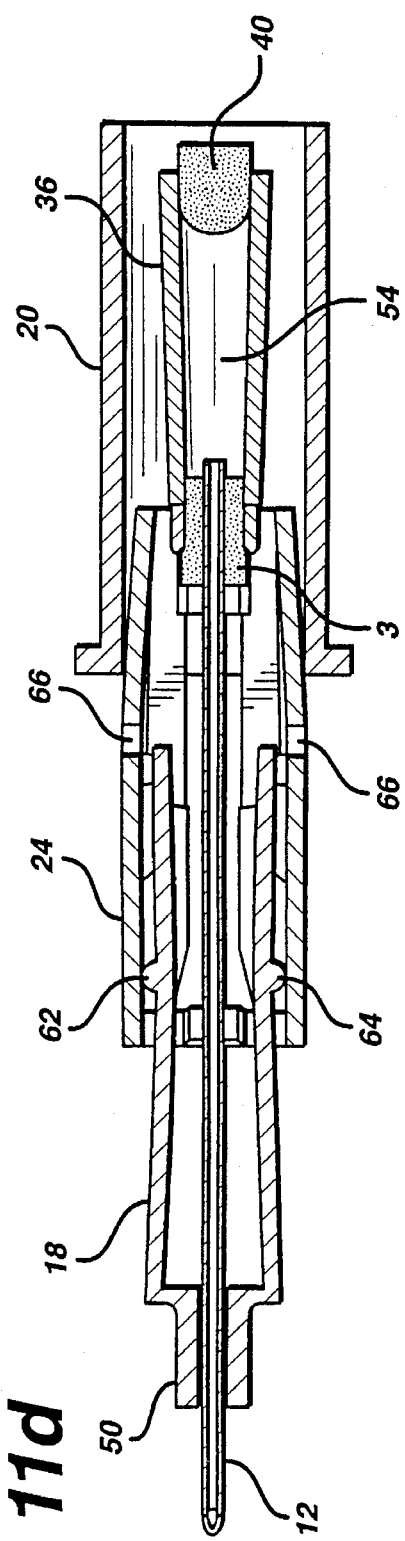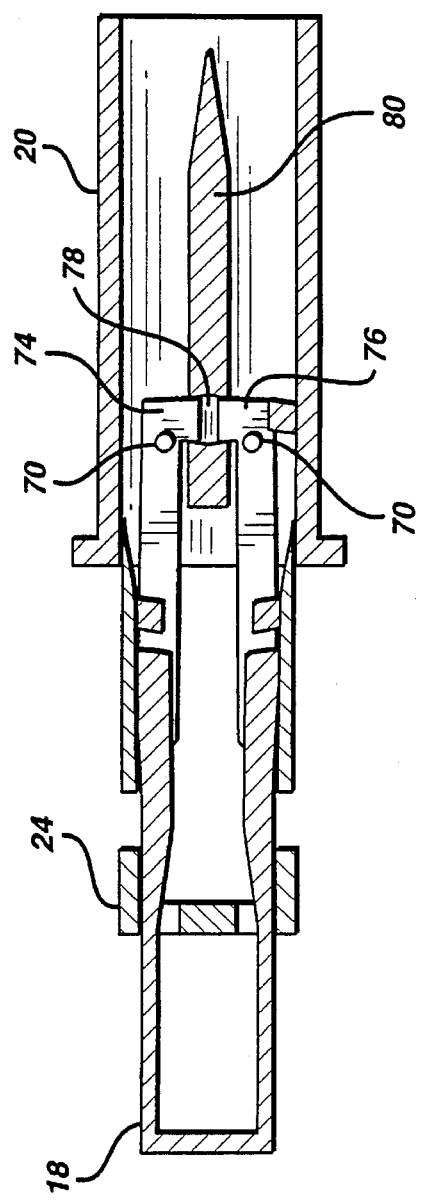

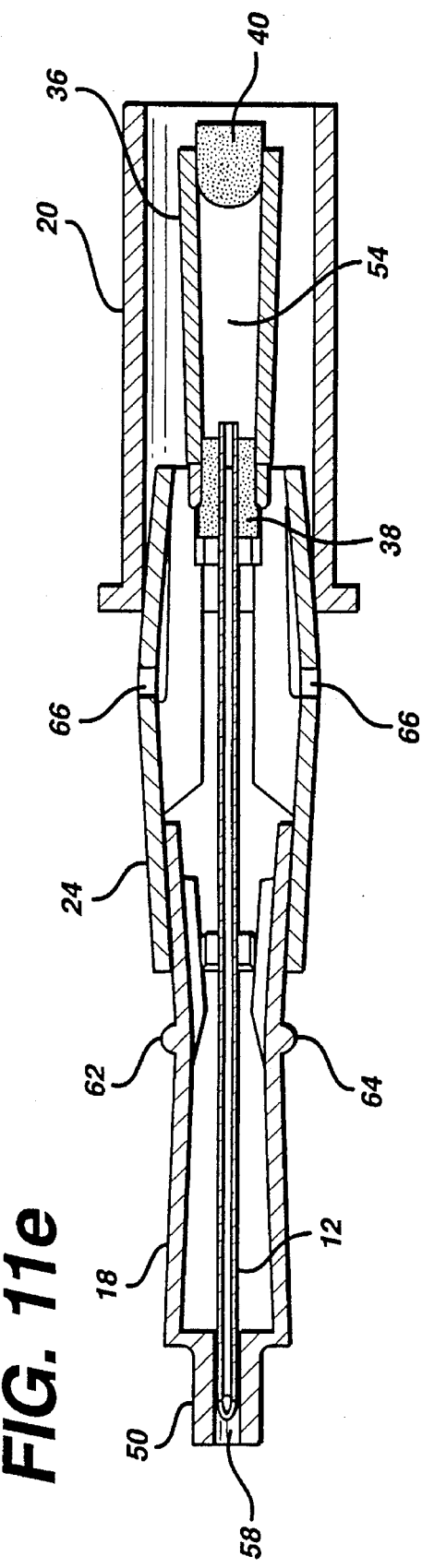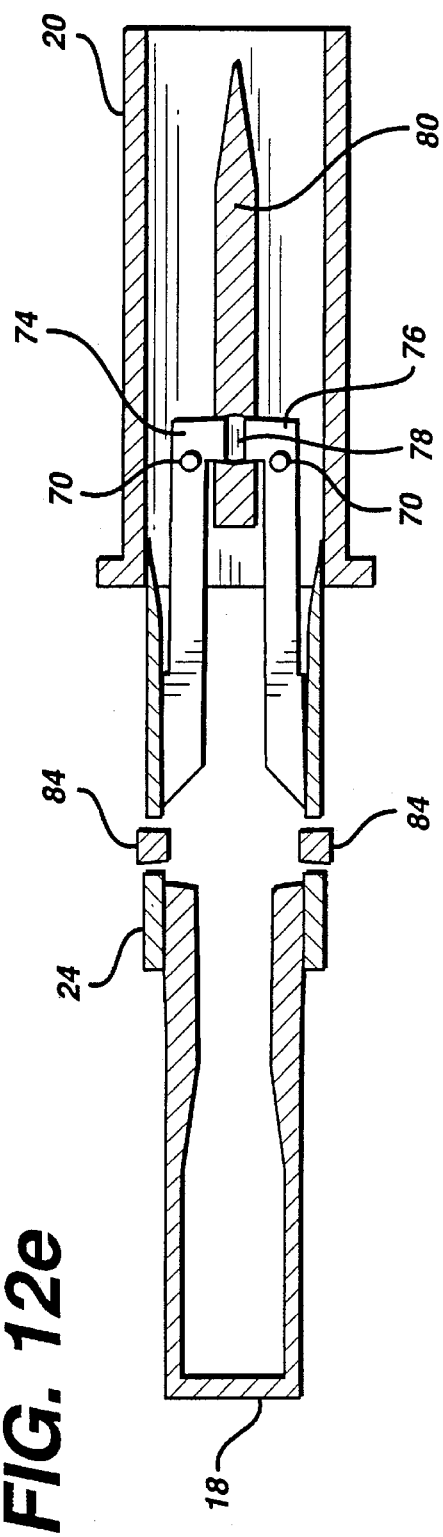
FIG. 11e
FIG. 12e

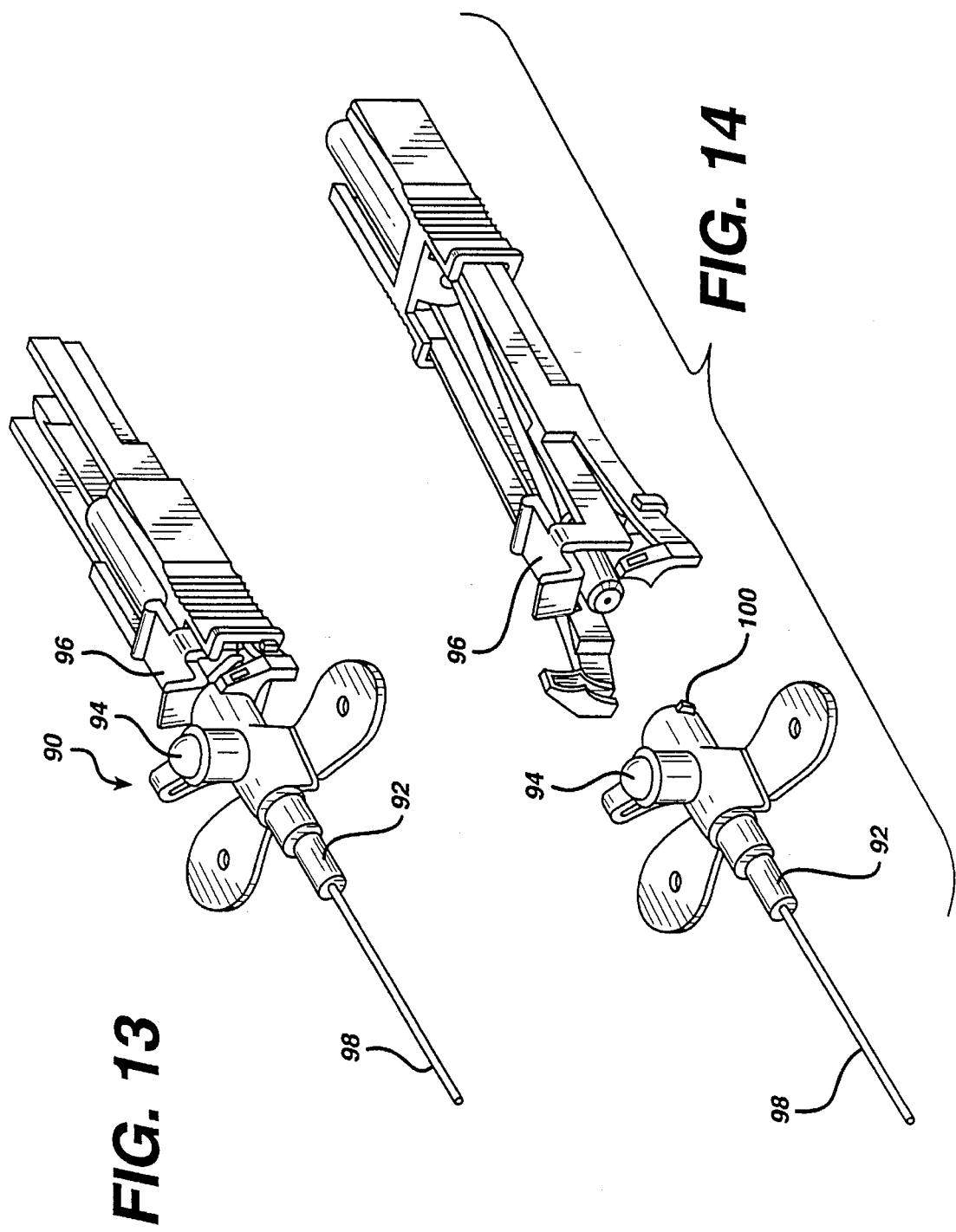

CATHETER ARRANGEMENT WITH INTERLOCKING SEQUENCED GUARDING MEMBERS FOR PROTECTING CANNULA

BACKGROUND OF THE INVENTION

1. Field of the Invention

The present invention relates, in general, to intravenous catheter insertion devices, and in particular pertains to a catheter needle tip protector and a safety mechanism which provides fail-safe protection for clinical personnel against the possibility of accidental punctures by a used IV cannular needle through automatic catheter needle tip protecting structure operative upon withdrawal of the cannular from a venipuncture the body of a patient.

In particular, pursuant to specific aspects of the invention, there is provided a catheter insertion device incorporating interlocking sequenced guarding members which are capable of being utilized in a considerable variety and types of catheter insertion devices. In essence, an important consideration which must be given to the aspect that there is a present safeguard in essentially a "fail-safe" arrangement, whereby the used cannula is fully retracted into its protective structure or housing prior to disengagement thereof from a catheter hub. Hereby, it has been noted that, upon occasion, needle stick of users of the device may be encountered in that the needle tip of the used cannula may still protrude to some extent, and resultingly pose a danger or hazard to clinical personnel or physicians using the catheter insertion device during separation of the cannula assembly from the catheter and its attached catheter hub. In numerous constructions and designs of catheter insertion devices, for example, such as the currently employed so-called Luer lock versions or sideport catheters, various techniques and structures are employed for separating retracted used cannulas and their associated housings and protective structures from the respective catheter and catheter hub portion, the former of which is still inserted in the venipuncture formed in the body of a patient and which is adapted to be connected to various other sources of parenteral fluids, blood, medications and the like during intravenous fluid supplying procedures, as is well known in the medical technology.

An important aspect of the invention resides in being able to ensure that the structure of the housing and telescopable sequencing guards for the used cannula or hollow needle which is being retracted will impart a clear indication as to the efficacy of full retraction of the cannula, thereby ensuring not only visual but also audible assurance of such protective procedures having been implemented during the catheter and cannula separation process, and prior to the effecting of the release of the housing or structure protectively containing the used cannula from the catheter hub.

Pursuant to a particular aspect of the invention, which may be applicable to various types of catheter insertion devices as described hereinbelow, there is provided a structure comprising interlocking sequenced guarding members whereby in a plurality of telescoping steps, the cannula, comprising the hollow needle, may be retracted into the guarding members in a step-by-step relationship as the guarding members are telescopingly extended relative to each other so as to ultimately provide a multiple locking system generating sequentially generated audible sounds or "clicks" informing clinical personnel operating the catheter device that the cannula has, in fact, been fully retracted and protectively locked in place, and consequently will no longer pose any physical danger or hazard to the user or clinical personnel, thereby enabling the completing of safe separation of the needle or cannula-housing structure from the catheter hub.

The utilization of clinical apparatus in which pointed hollow needles or cannulas are employed in order to puncture the skin of a patient, and especially catheters utilizing such needles to effectuate venipunctures, is well known in the medical art and is widely practiced by physicians and clinical personnel for the purpose of injecting fluids and drugs directly into the bloodstream of patients. Additionally, during surgical operations or procedures it may be frequently required that whole blood transfusions and parenteral fluids be administered to a patient undergoing such surgical procedures. Basically, as is well known and has been employed for a considerable length of time, the introduction of such fluids into the cardiovascular systems of patients has necessitated the forming of a venipuncture utilizing a hollow rigid needle having a proximal attachment site for a fluid connection which is adapted to interconnect the needle with a source of intravenously administered fluids.

The foregoing method of administering fluids to patients through venipunctures has been subject to some rather serious problems in the administration of fluids to patients in this medical technology. Thus, a primary concern which had to be addressed resided in the inherent rigidity of the needle, the latter of which is normally generally constituted of surgical-quality steel, and while inserted into the vein of a patient, necessitated the needle to be maintained for reasons of safety in a fixed position at the general site of the venipuncture throughout the duration of fluid administration or transfusion, whereby such a procedure could conceivably consume a considerable length of time. In addition to the foregoing, at times it has been necessary to periodically draw blood samples and/or successively administer intravenous fluids to a patient, thus requiring the patient to be subjected to a series or plurality of venipunctures, each administered at a specific time and at different sites on the body, resulting in a relatively traumatic experience to the patient in view of such repeated and somewhat painful and unpleasant venipunctures.

In order to ameliorate or possibly even eliminate the foregoing problems, in the medical technology it has been more recently the practice to introduce a flexible tubular catheter of a low-friction material, such as a silastic or Teflon into the vein of a patient and to permit the catheter tube to remain in such a position over lengthier periods of time for purposes of; for example, periodically administering fluids, including parenteral fluids, blood/plasma transfusions, medications in liquid form and also for the collection of blood samples and the like. In this manner, the previously encountered trauma, extravasation, and infiltration caused by repeated venipunctures have been largely avoided, and the danger and discomfort to a patient of leaving a rigid needle in the body for a prolonged period of time has been generally overcome. Thus, in order to position the distal end of such a flexible catheter tube within the body cavity of a patient, such as a vascular cavity or vein, there is normally employed a cannula or hollow sharp-tipped needle for the purpose of forming the venipuncture. Thereafter, the flexible catheter tube, which is telescopically and slidably coaxially mounted on the outer circumference of the cannula or hollow needle so as to extend sleeve-like thereabout is advanced along the length of the needle into the vein subsequent to the needle having formed the venipuncture. Thereafter, the needle is adapted to be withdrawn from the interior of the catheter tube, while permitting the latter to remain within the body of the patient at the site of the venipuncture, and the needle is suitably discarded.

Inasmuch as the needle which has been previously positioned in the body of the patient upon forming the venipuncture may have been exposed to infectious agents; for instance, such as a patient infected with the Acquired Immune Deficiency Syndrome (AIDS) which is frequently or practically always ultimately fatal in nature, or other dangerous infectious conditions such as hepatitis, there is present the danger or hazard that the clinical personnel may inadvertently or accidentally jab or stick themselves with the used needle after withdrawal from the body of the patient, with the possibility of infection or even death resulting therefrom.

2. Discussion of the Prior Art

Although extendable or telescoping elements for protecting used cannulas of catheter insertion devices are currently known in the art, none of these provide for the use of interlocking sequenced telescoping guarding-members for the "fail-safe" retraction and protection of the cannulas.

Thus, U.S. Pat. No. 4,950,252 to Luther et al. discloses a cannula guard and housing structure which are mutually relatively axially extendable for receiving therein a used cannula in a protective environment.

McDonald U.S. Pat. No. 4,944,725 addresses the problem in disclosing an intravenous catheter which incorporates a structure for protecting a clinician or physician from accidental puncture which may result in the transfer of dangerous infections from the patient. The catheter is introduced into the patient's body with the aid of a needle of hollow or cannula construction which is thereafter withdrawn from the patient's body into a protective housing in the absence of exposing the needle during any intermediate stage of the withdrawing process. The housing is then latched in place subsequent to needle withdrawal, and for unlocking a catheter hub in place subsequent to the time, and effecting withdrawal and locking in one continuous motion.

Another publication which is applicable to providing for the protection of the point of a needle subsequent or upon removal thereof from the body of a patient is disclosed in Dombrowski et al. U.S. Pat. No. 4,790,828, wherein a nose portion or cap is tethered to a housing by means of a collapsible tethering structure encompassing the needle such that the needle will be retracted into a sheath-like expanding arrangement which will securely prevent potential injury to clinical personnel caused by being jabbed by an exposed used point of a needle.

SUMMARY OF THE INVENTION

Accordingly, in order to provide an improved structure in the provision of a protecting arrangement for a used cannula, and especially a safety mechanism which will ensure a practically "fail-safe" operation, the present invention contemplates the provision of telescopically sequentially movable guarding members in the form of sleeves or housing whereby locking devices provide for the locked extension of the cannula prior to its use in guiding a catheter into the vein of a patient, and thereafter, when it is desired to retract the cannula, while the components remain in a locked condition, there is effected a first extension step whereby an outer housing sleeve passes beyond a detent in one of the guarding members, thereafter in a second step permitting unlocking between the inner guarding members, and enabling the housing sleeve to be further extended rearwardly while a second two-way lock is in an unlocked position; and in a further step, while the initial locking structure remains unlocked and the second remaining locking structure is also in an unlocked condition, to facilitate further complete extension between the sequenced interlocking guarding members in which the forward guarding member in which locked into the back guarding member, and the back guarding member is locked into the sleeve-like housing so as to fully encompass the cannula.

Accordingly, it is an object of the present invention to provide a catheter insertion device providing for a "fail-safe" retraction of a used cannula into a sequenced telescopable guarding arrangement or structure.

A more specific object of the invention is to provide a guarding structure into which a used cannula may be retracted prior to separation of the structure from a catheter, and in which, through a plurality of releasably locked interconnecting sequenced guarding members, this will ensure the complete and safe retraction of the cannula into a protective environment.

Another object of the present invention resides in the provision of a catheter insertion device of the type described in which the interlocking sequenced guarding members enabling the complete retraction of a used cannula will effectuate the latter function through the sequential disengagement and/or engagement of a plurality of axially spaced locking devices, each such locking device providing for an audible indication as to the efficacy of the locking action so as to apprise the user of the complete retraction of the cannula having taken place.

BRIEF DESCRIPTION OF THE DRAWINGS

Reference may now be had to the following detailed description of exemplary embodiments of the invention, taken in conjunction with the accompanying drawings; in which:

FIGS. 11a through 11e illustrate, respectively, various operative positions of the interlocking sequenced telescopable guarding members of FIGS. 3 through 10, taken along Line 11—11 in FIG. 4;

FIGS. 12a through 12e illustrate views similar to those of FIGS. 11a through 11e taken along Line 12—12 in FIG. 4;

FIG. 13 illustrates a perspective view of a further embodiment of a catheter sideport insertion device, shown with the cannula in the fully extended operative position; and FIG. 14 illustrates, in an exploded perspective view, the catheter insertion device of FIG. 13 with the cannula in its fully retracted position and the catheter sideport portion having been separated therefrom.

DETAILED DESCRIPTION OF PREFERRED EMBODIMENTS

Figure 1:
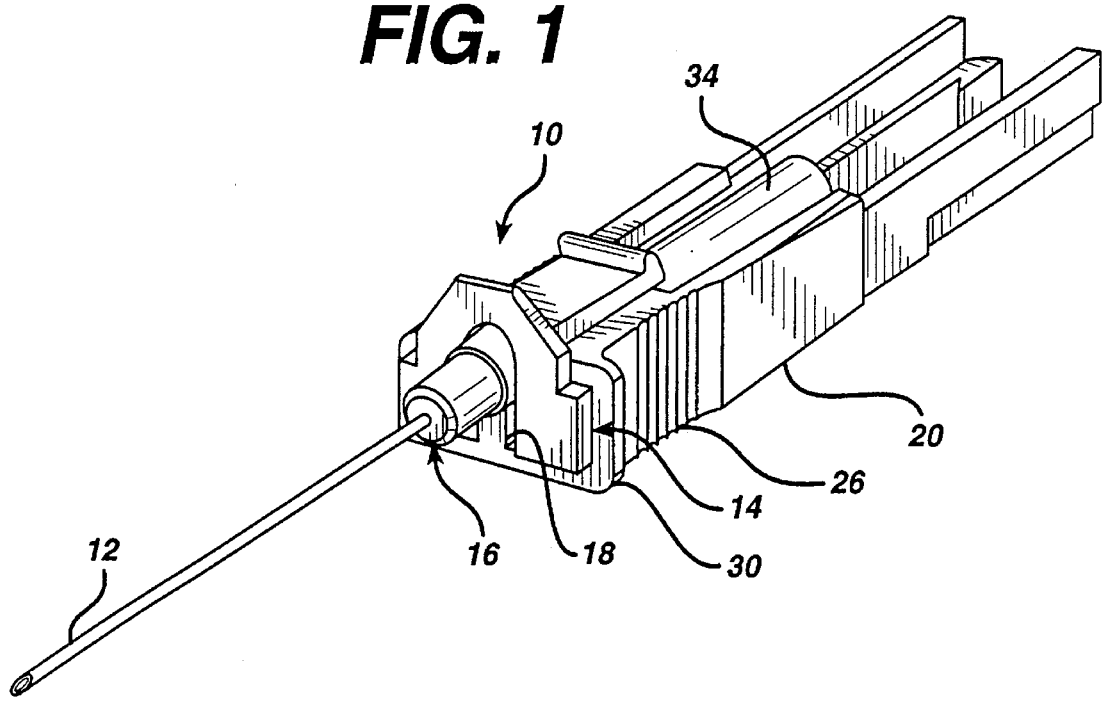
FIG. 1 illustrates a perspective view of a first embodiment of a catheter insertion device, shown with the cannula in the fully extended operative position thereof.

Referring now in detail to FIG. 1 of the drawings, there is illustrated, generally diagrammatically, a perspective view of a catheter insertion device 10 wherein the cannula 12 thereof is locked in its fully extended operative position and in which a push-tab 14 and nose guard 16 are arranged on a forward cannula guarding member 18 which is adapted to be slid or extended, as described hereinbelow, from a housing 20, in this instance containing a blood chamber 22.

As illustrated in FIG. 1, the catheter insertion device 10 also includes the nose guard 16 through which the cannula 12 extends in a slidable manner, and wherein a second or back guarding member 24 is arranged telescopically within the forward guarding member 18 and is also adapted to be positioned within the housing 20. As represented, the housing 20 includes finger-engaging surfaces 26 on opposite sides thereof (only one shown) which may be ribbed in nature to prevent the fingers of a user or clinical personnel from slipping off during use and also for holding the device in a good gripped position during insertion of the cannula 12 or hollow needle tip thereof into the body of a patient so as to effect a venipuncture. The nose guard is adapted to mate with a catheter hub 30 which may be in the nature of an element containing a Luer lock lug structure, and which has a catheter tube closely and slidably extending over the outer surface of the cannula 12, the catheter tube being flexible in nature and constituted of a low friction plastic material, such as Teflon or the like, as is well known in the medical technology.

Figure 2:
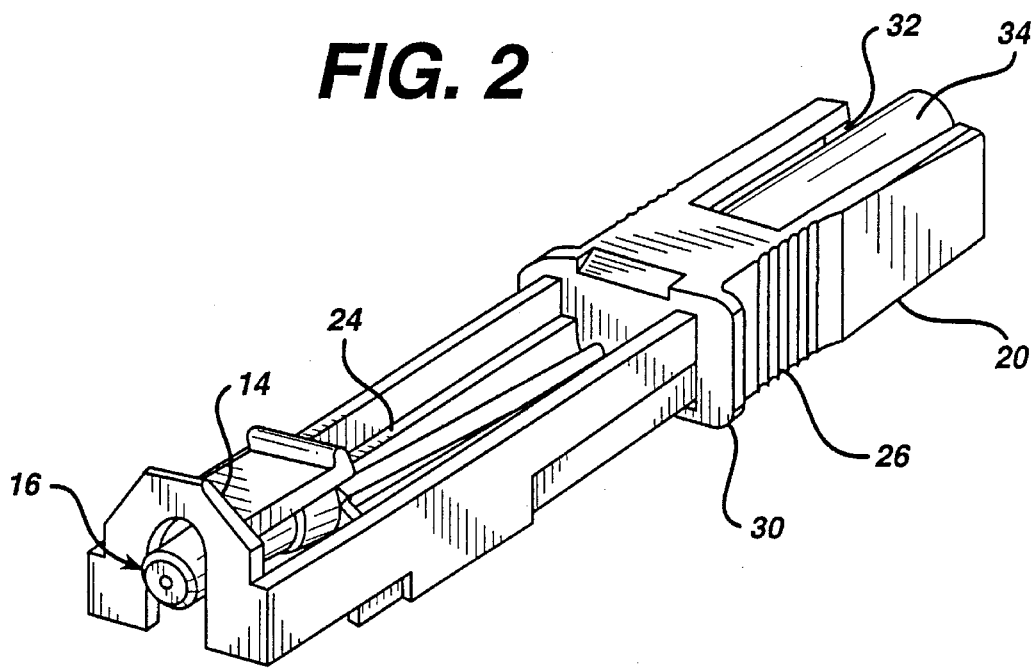
FIG. 2 illustrates a view similar to FIG. 1 illustrating the cannula in the fully retracted and guarded position within the device.

As illustrated in FIG. 2 of the drawings, upon the catheter having been extended over the cannula 12 into the venipuncture formed in the patient's body, the cannula is then withdrawn to a fully guarded position within the cannula assembly, and there also enabling separation therefrom of the catheter hub 30 and the catheter tube extending into the vein of the patient at the puncture site. This separation may be effected in numerous ways depending upon the type of catheter insertion device employed and; for example, in various cases may be as disclosed in the embodiments of catheter insertion devices disclosed in copending U.S. patent application Ser. No. 08/483,949 (Attorney's Docket No. 9695), which is commonly assigned to the assignee of the present application and the disclosure of which is incorporated herein by reference. In that instance, as disclosed in the copending above-referenced application, various mechanisms are described for the purpose of releasing and separating the cannula assembly containing the cannula retracted therein in a guardedly protective position from its connection to a catheter hub and attendant catheter, whereby the catheter hub may incorporate a component of a Luer lock or the like. This separation between the components may be implemented by means of a lever and clip element which is pivotable or tiltable in various orientations as described therein, or through the actuation of a suitable push-tab and guard element.

Figure 3:
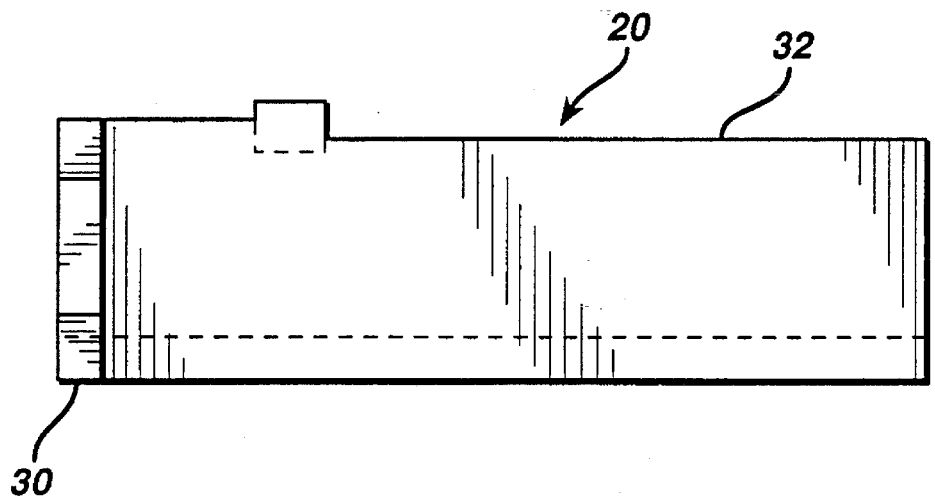
FIG. 3 illustrates a side view of a housing member of the cannula assembly.
Figure 4:
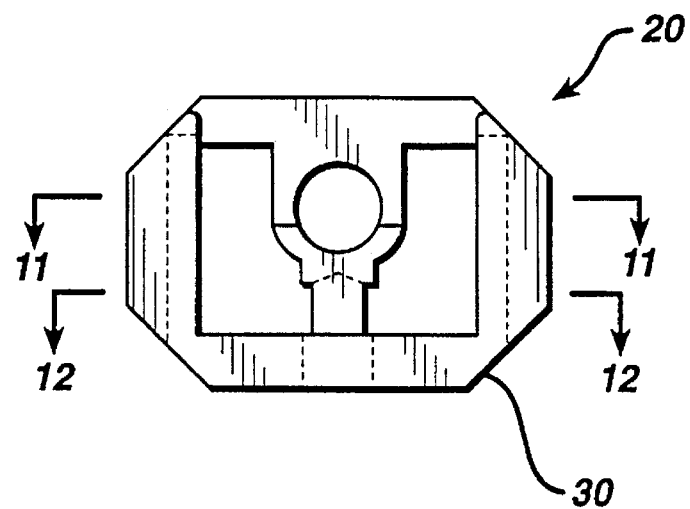
FIG. 4 illustrates a front end view of the housing member of FIG. 3.

As disclosed herein, having reference to FIGS. 3 and 4 of the drawings, the housing 20 is essentially an elongated hollow rectangular member having a front wall structure 30 and an upper longitudinally extending wall opening 32 through which there can be viewed a blood chamber 34 located therein, the latter of which is in communication with the lumen of the cannula 12, and wherein a slidable insert 36 of generally cylindrical or tubular configuration incorporates sealing elements 38, 40 at both ends thereof so as to close in a quantity of blood from the body of the patient.

Figure 5:
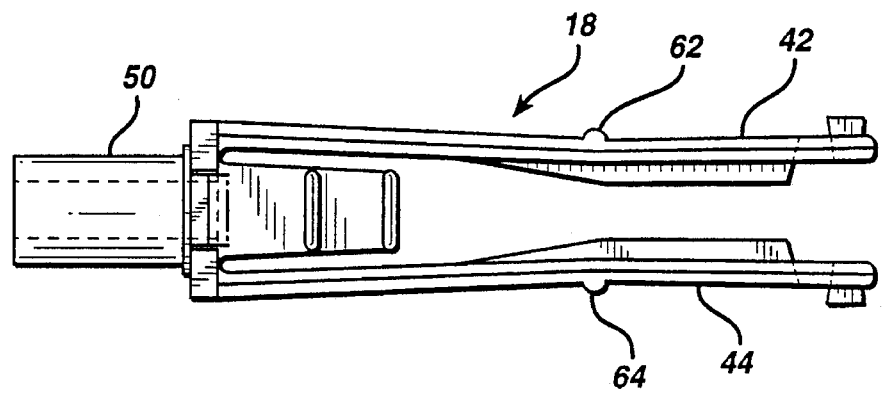
FIGS. 5, 6 and 7 illustrate, respectively, top, side and front end views of a forward guarding member for the cannula.
Figure 6:
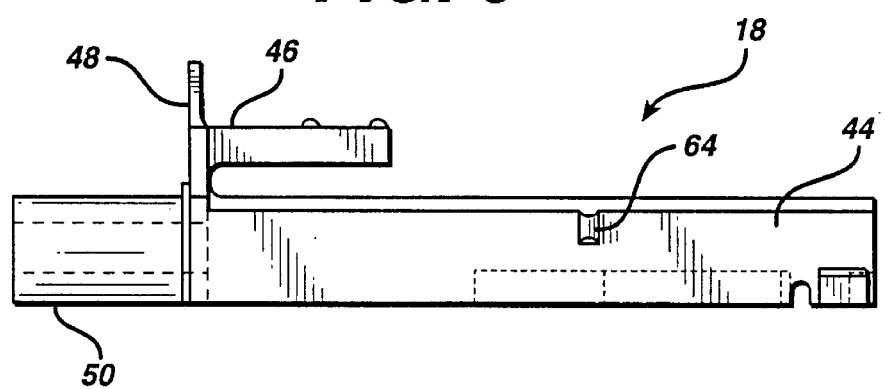
Figure 7:
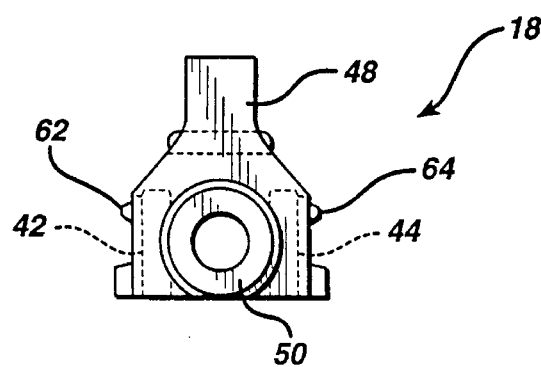
Figure 8:
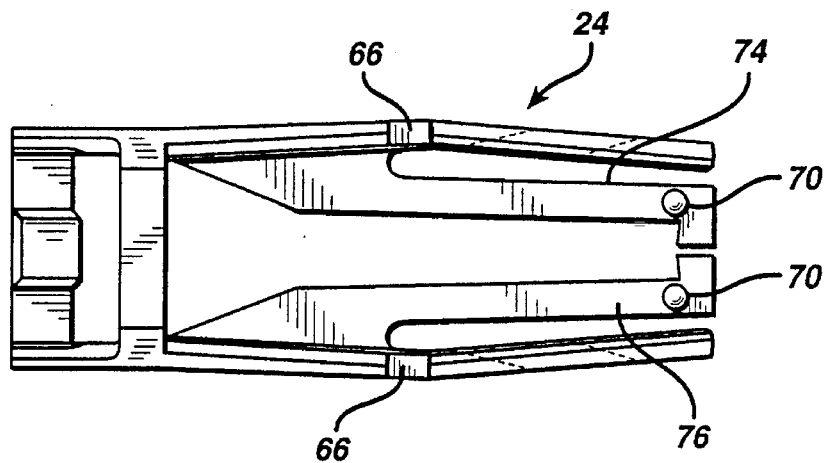
FIGS. 8, 9 and 10 illustrate, respectively, top plan, side and front end views of a back guarding member adapted to be operatively and telescopingly associated with the housing member and the front guarding member of the cannula assembly structure.
Figure 9:
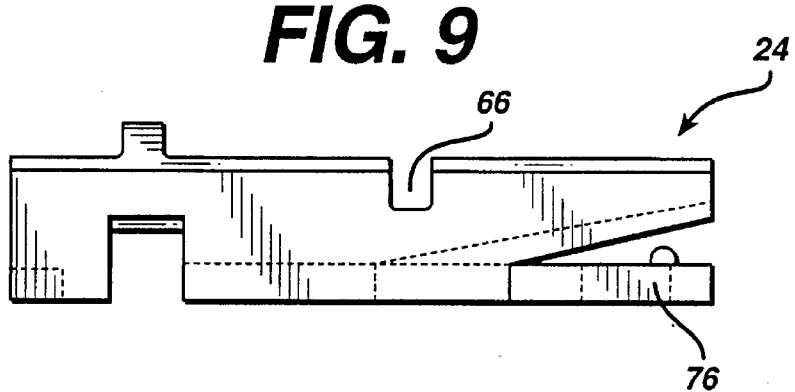
Figure 10:
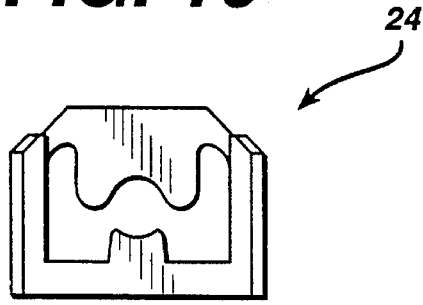
Figure 11C:
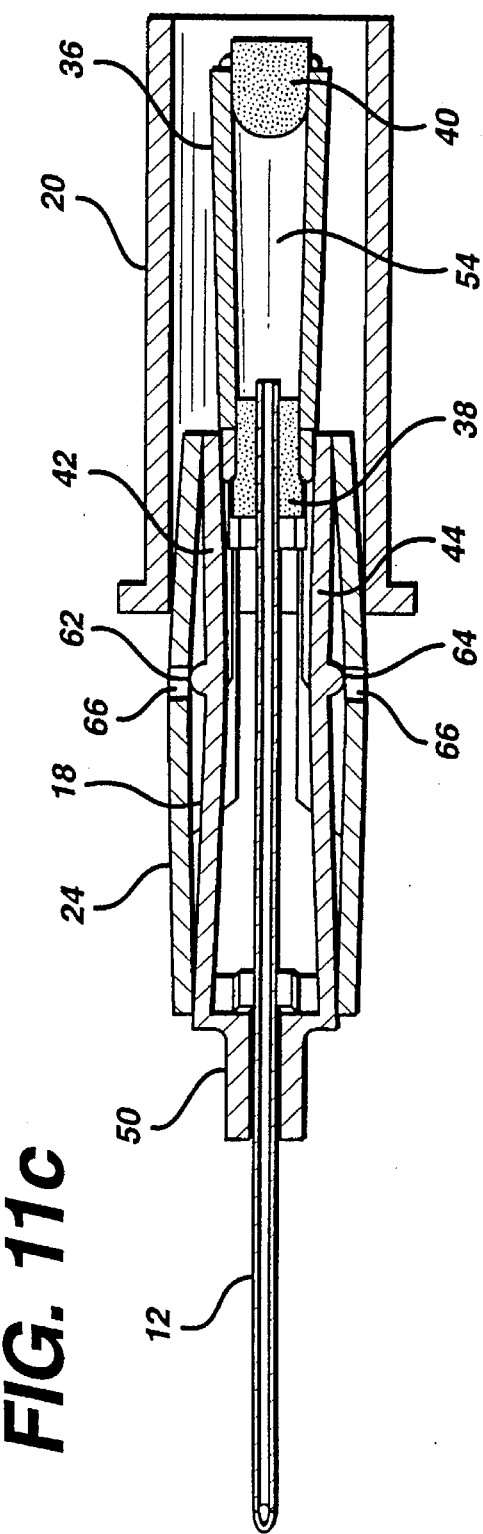
Figure 12C:
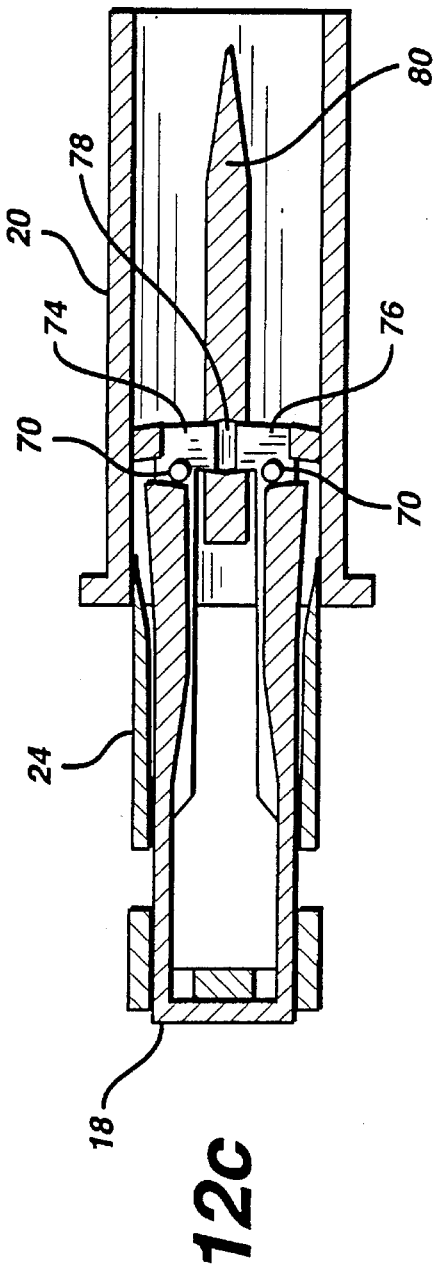

The forward or front guarding member 18 is of a generally bifurcated structure of having two generally flat parallel spaced sidewalls 42, 44 and wherein an upper push-tab structure 46 and forward tab or plate 48 are integrally formed therewith, and which extends into a nose guard 50, as shown in FIGS. 5 to 7 of the drawings. Various configurations of this particular nose guard member and cannula tip protector may be utilized, and other designs without the nose and cannula tip protector may also be contemplated for other types of catheter insertion devices or Luer lock-catheter structures.

The rear or back guarding member 24 is adapted to be slidably disposed in telescopable relationship over the forward guarding member 18 and includes a longitudinal passageway into which the bifurcated sidewall members 42, 44 can slidably enter so as to allow for telescoping relatively slidable movement between the guarding members. These members 18, 24 are insertable into the longitudinal extent of the housing 20, as shown in FIGS. 1 and 2 of the drawings, and the operative latching function of which is clearly described with reference to FIGS. 11a through 11e and FIGS. 12a through 12e of the drawings.

With respect to the function of the interlocking sequenced or telescopingly movable guarding members 18 and 24, reference may now be had to FIG. 1 of the drawings, whereby FIGS. 11a and 12a illustrate sectional views of the components in the position whereby the cannula 12 is locked in its fully extended operative condition adapted to be inserted into the vein of a patient. Hereby, the proximate end of the catheter extends through seal 38 so as to be in communication with a cylindrical chamber 54 formed by the cylindrical insert 36, and the opposite end of which is closed by the further sealing element 40 so as to be able to receive and store blood, if necessary, from the vein of a patient.

The housing 20 is illustrated as having the rear or back guarding member 24 entirely fully positioned therein, and with the front or forward guarding member 18 being essentially completely positioned within the back guarding member 24. The forward guarding member 18 has the nose piece or guard 50 adapted to extend into a catheter hub (not shown), and which includes a passageway 58 through which the cannula 12 may readily pass in slidable operation. A seal 60 may be provided so as to encompass the extent of the cannula 12 at that location.

In the position shown in FIGS. 11a and 12a, a pair of lugs 62, 64 protruding from the outer diameter of the forward guarding member 18 each engage into respective detents 66 formed in the periphery of the back guarding member 24, and which are positioned in alignment therewith so as to prevent relative axial and rotational motion therebetween.

At that point in time, the rear portion of the forward guarding member 18 has its inwardly extending lugs 70 on the bifurcated arms unlatched relative to the remaining cannula components.

When effecting the initial retraction of the used cannula 12 upon withdrawal from the vein of the patient into the cannula assembly, as shown in FIGS. 11b and 12b of the drawings, the forward and back guarding members 18, 24 are still in a mutually locked position, while the housing 20 is pulled backwards by being manually engaged at its gripping surfaces so as to draw therewith the cannula 12 and the chamber at the distal end thereof which communicates with the cannula 12.

In a third extension step, upon further movement of the housing member and the cannula, the outwardly extending protrusions or lugs 62, 64 on the forward guarding member 18 disengage from the detents 66 in the back guarding member, since the bifurcated sidewalls 42, 42 are deflected outwardly at that location, being essentially elastically resilient in nature. This releases the forward guarding member 18 from the back guarding member 24 at the same time, which causes the back guarding member 24 to be locked in the housing 20, with the aid of the locks 74, 79 at the rear of the guarding member.

In a fourth step, the housing 20 is still further retracted and whereby there is an unlocked condition present between the two guarding members 18, 24 enabling these to be telescopically extended apart.

Upon the final condition of telescopic extension having been reached by the components 18, 24 and 20, as shown in FIGS. 11e and 12e of the drawings, the protuberances or lugs 62, 64 on the forward guarding member 18 are in an exposed condition, whereas the two-way lock 74, 76 snaps into detents 78 in an internal guide rib 80 formed in the housing 20, and concurrently the back guiding member 24 is latched to the housing 20 by another two-way lock 84. In that position of the members 18, 24 and housing 20, as illustrated in FIGS. 11e and 12e, the cannula 12 is entirely retracted within the cannula assembly consisting essentially of the forward guarding member 18, the back guarding member 24 and the housing 20, which are telescoped in the extended position shown in FIGS. 2, 11e and 12e of the drawings, whereupon it is then possible to effectuate the release of the catheter hub from the nose guard end of the cannula assembly, as mentioned hereinabove and as disclosed in the copending U.S. patent application Ser. No. 08/483,949.

Referring to FIGS. 13 and 14 of the drawings, this illustrates a modified catheter insertion device 90, which is primarily a sideport catheter, wherein the catheter hub 92 includes an openable sideport 94 for adding further fluids or medications to the parenteral fluid being conducted through the catheter into the vein of a patient.

In this instance, there is provided a push-tab 96 for Luer lock release, which is adapted to disengage the cannula structure 98 from the catheter hub 92, the latter of which includes Luer lock lugs 100 formed thereon. For the remainder, the structure of the housing and the telescopably extendable forward and back guarding members are essentially analogous or similar in structure and function with those described with regard to the embodiment of the catheter insertion device shown in FIG. 1 of the drawings. Hereby, with respect to the embodiment of FIG. 13 relative to the sideport catheter construction, this shows the catheter hub having been separated through actuation of the push-tab 96 for the Luer lock so as to disengage the lugs 100 on the catheter hub 92 and to permit the entire cannula assembly with the therein retracted and guarded cannula to be discarded.

The foregoing provides for a completely dependable and essentially "fail-safe" retraction of a used cannula or hollow needle into a guarding structure so as to prevent any hazard to clinical personnel or any users by jabbing or sticking themselves with the tip of the needle.

The telescopable forward and back guarding members 18, 24 in conjunction with the housing 20 may be utilized for numerous types of catheter injection devices, whereby the devices may be separated from a catheter hub or Luer lock by either actuating a lever and clip construction, or in any other suitable manner pursuant to the technology.

The components may be essentially formed of simple molded parts and from inexpensive plastics, as is well known and currently employed in the medical technology.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. An arrangement for protecting a cannula of a catheter insertion device, comprising:
    (a) a housing for receiving a cannular needle, said cannular needle extending from an end of said housing and being adapted to administer a catheter to a patient;
    (b) needle guarding means slidably mounted on said housing, said cannular needle extending through said needle guarding means in the operative position of said cannular needle, said needle guarding means comprising:
        (i) a back guarding member slidably mounted in said housing; and
        (ii) a forward guarding member slidably mounted in said back guarding member, said forward guarding member being retracted into said back guarding member and said back guarding member being retracted into said housing in the operative condition of said cannular needle, and said back guarding member and said forwarding guarding member being telescopically extendable relative to each other and said housing so as to form a protective containment for said cannular needle upon the withdrawal thereof from the body of the patient.

2. An arrangement as claimed in claim 1, wherein said housing comprises an elongate rectangular structure having one open end and one open side, and a central longitudinal rib extending within said housing.

3. An arrangement as claimed in claim 2, wherein said back guarding member comprises an open-ended elongate rectangular structure slidably insertable into said housing for axial displacement relative thereto.

4. An arrangement as claimed in claim 3, wherein said forward guarding member comprises a pair of parallel extending arms connected at one end thereof so as to form a bifurcated structure, said arms being slidably insertable into said back guarding member for axial displacement relative thereto.

5. An arrangement as claimed in claim 4, wherein protruding lugs on outer surfaces of said forward guarding members latchingly engage detents in said back guarding member in the retracted position of said guarding members within said housing.

6. An arrangement as claimed in claim 5, wherein in a first partially extended condition of said arrangement, said guarding members are partly extended from said housing while said protruding lugs remain latchingly engaged in said detents so as to inhibit relative axial movement between said guarding members.

7. An arrangement as claimed in claim 6, wherein in a second further partially extended condition of said arrangement, said protruding lugs are disengaged from said detents, said forward guarding member being partly extended from said back guarding member.

8. An arrangement as claimed in claim 7, wherein in a third further partially extended condition of said guarding members, locking means in said back guarding member latchingly engage recesses in the longitudinal rib of said housing for locking said housing and back guarding member in extended position relative to each other.

9. An arrangement as claimed in claim 8, wherein in a fully extended condition of said arrangement, said forward guarding member is further extended relative to said back guarding member; and latching means engaging said guarding members so as to maintain said guarding members in the fully extended condition whereby said cannular needle is completely retracted into said guarding members.

10. An arrangement as claimed in claim 8, wherein said locking means are disengaged from said recesses in the retracted and first partially extended positions of said guarding members.

11. An arrangement as claimed in claim 9, wherein the latching action between said protruding lugs and detents and the latching action of said locking means and latching means each generate a predetermined audible sound indicative of a specific condition in the sequenced extension of said guarding members.

12. An arrangement as claimed in claim 4, wherein said forward guarding member includes a nose guard for connection with the catheter hub of a catheter.

13. An arrangement as claimed in claim 1, wherein said housing, said forward guarding member and said rear guarding member are each constituted of a plastic material.

* * * * *

(12) EX PARTE REEXAMINATION CERTIFICATE (8134th)
United States Patent
Bogert

(10) Number: US 5,562,631 C1
(45) Certificate Issued: Apr. 5, 2011

(54) CATHETER ARRANGEMENT WITH INTERLOCKING SEQUENCED GUARDING MEMBERS FOR PROTECTING CANNULA

(75) Inventor: David L. Bogert, Plainville, CT (US)

(73) Assignee: Smiths Medical ASD, Inc., Rockland, MA (US)

Reexamination Request:
No. 90/010,350, Feb. 21, 2009

Reexamination Certificate for:
Patent No.: 5,562,631
Issued: Oct. 8, 1996
Appl. No.: 08/483,950
Filed: Jun. 7, 1995

(51) Int. Cl.
*A61M 5/00* (2006.01)

(52) U.S. Cl. ........................ 604/192; 604/263
(58) Field of Classification Search ........................ None
See application file for complete search history.

(56) References Cited

U.S. PATENT DOCUMENTS

| | | | | |
|---|---|---|---|---|
| 4,897,083 A | * | 1/1990 | Martell | ........................ 604/192 |
| 4,944,725 A | | 7/1990 | McDonald | |
| 4,950,252 A | | 8/1990 | Luther et al. | |
| 5,102,394 A | * | 4/1992 | Lasaitis et al. | ......... 604/164.08 |
| 5,688,249 A | | 11/1997 | Chang et al. | |
| 5,704,919 A | | 1/1998 | Kraus et al. | |

FOREIGN PATENT DOCUMENTS

| | | |
|---|---|---|
| EP | 0576302 A1 | 12/1993 |
| EP | 0747084 B1 | 4/2001 |
| WO | 9413341 | 6/1994 |
| WO | 9308865 | 12/2008 |

\* cited by examiner

*Primary Examiner*—Jeanne M Clark

(57) ABSTRACT

A catheter needle tip protector and a safety mechanism which provides fail-safe protection for clinical personnel against the possibility of accidental punctures by a used IV cannular needle through automatic catheter needle tip protecting structure operative upon withdrawal of the cannular from a venipuncture the body of a patient.

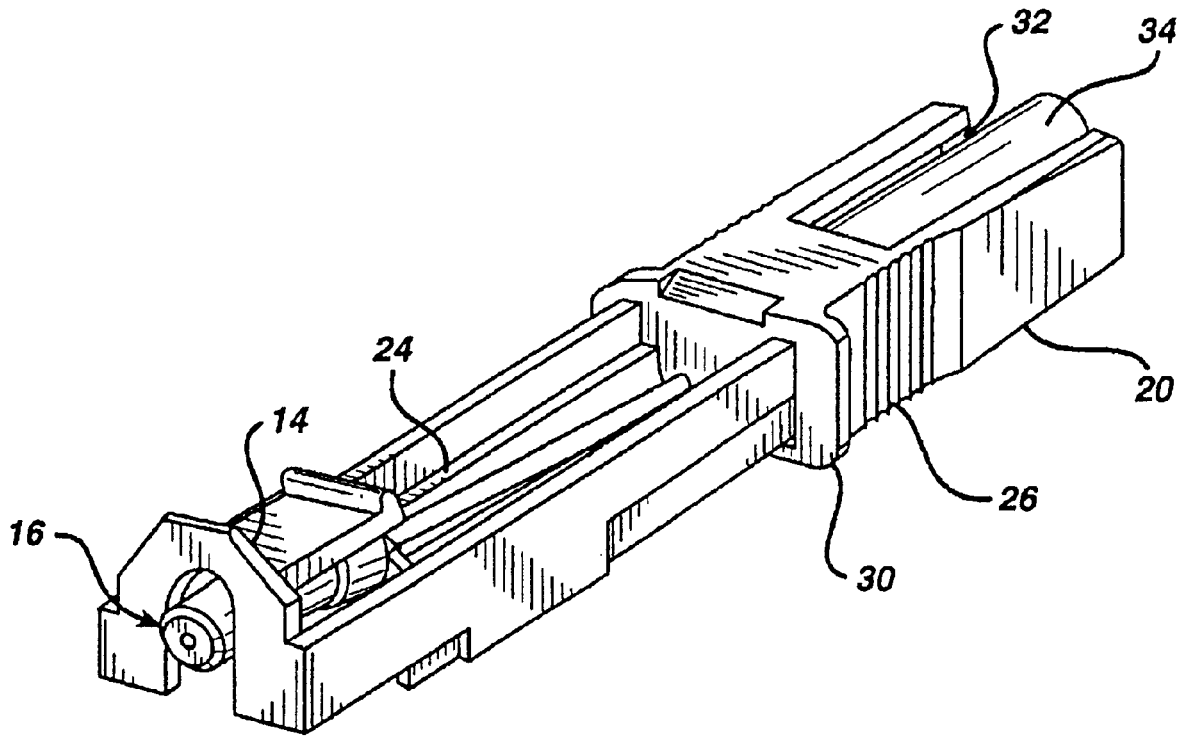

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claim 1 is cancelled.

Claims 2-13 were not reexamined.

* * * * *